US007182956B2

(12) United States Patent
Perricone et al.

(10) Patent No.: US 7,182,956 B2
(45) Date of Patent: *Feb. 27, 2007

(54) STABLE TOPICAL DRUG DELIVERY COMPOSITIONS

(75) Inventors: Nicholas V. Perricone, 377 Research Pkwy., Meriden, CT (US) 06450; Chim Potini, Bloomington, IL (US)

(73) Assignee: Nicholas V. Perricone, Meriden, CT (US)

( * ) Notice: Subject to any disclaimer, the term of this patent is extended or adjusted under 35 U.S.C. 154(b) by 154 days.

This patent is subject to a terminal disclaimer.

(21) Appl. No.: 10/749,914

(22) Filed: Dec. 31, 2003

(65) Prior Publication Data

US 2004/0197391 A1 Oct. 7, 2004

Related U.S. Application Data

(63) Continuation-in-part of application No. 10/448,632, filed on May 30, 2003.

(60) Provisional application No. 60/437,279, filed on Dec. 31, 2002, provisional application No. 60/384,597, filed on May 31, 2002.

(51) Int. Cl.
- A61K 9/127 (2006.01)
- A61K 9/52 (2006.01)
- A61K 38/00 (2006.01)
- A61K 38/28 (2006.01)
- A61K 31/685 (2006.01)
- A61K 38/27 (2006.01)
- A61K 38/11 (2006.01)
- A61K 38/23 (2006.01)
- A61K 38/31 (2006.01)
- A61K 38/24 (2006.01)
- A61K 31/56 (2006.01)
- A61K 47/00 (2006.01)
- A01N 57/26 (2006.01)
- A01N 37/18 (2006.01)

(52) U.S. Cl. .............. 424/450; 424/400; 424/457; 514/2; 514/3; 514/78; 514/169; 514/177; 514/179; 514/772; 514/806; 514/807; 514/808; 514/866; 514/970

(58) Field of Classification Search .......... 424/450, 424/452; 514/3, 78, 970
See application file for complete search history.

(56) References Cited

U.S. PATENT DOCUMENTS

| | | | |
|---|---|---|---|
| 4,174,296 A | 11/1979 | Kass | 252/312 |
| 4,624,665 A | 11/1986 | Nuwayser | 604/307 |
| 4,687,661 A * | 8/1987 | Kikuchi et al. | 124/38 |
| 5,120,561 A | 6/1992 | Silva et al. | 426/531 |
| 5,674,912 A | 10/1997 | Martin | 514/724 |
| 5,874,479 A | 2/1999 | Martin | 514/724 |
| 5,985,298 A * | 11/1999 | Brieva et al. | 424/401 |
| 6,165,500 A | 12/2000 | Cevc | 424/450 |
| 6,211,250 B1 | 4/2001 | Tomlinson et al. | 514/772.4 |
| 6,214,375 B1 * | 4/2001 | Modi | 424/450 |
| 6,294,192 B1 * | 9/2001 | Patel et al. | 424/451 |
| 6,521,250 B2 | 2/2003 | Meconi et al. | 424/443 |
| 6,538,061 B2 * | 3/2003 | Chaiyawat et al. | 524/806 |
| 6,555,573 B2 | 4/2003 | Rosenbloom | 514/456 |
| 2004/0191305 A1 * | 9/2004 | Perricone et al. | 424/450 |

FOREIGN PATENT DOCUMENTS

WO WO 01/01963 A1 1/2001

OTHER PUBLICATIONS

Agarwal, R. and Katare, O.P., Preparation and In Vitro Evaluation of Miconazole Nitrate-Loaded Topical Liposomes, *Pharmaceutical Technology*, Nov. 2002, p. 48-60.
Benson, H. and Prankerd, R, "Optimization of Drug Delivery 4. Transdermal Drug Delivery," *Aus J Hosp Pharm*, 27(6): 441-448 (1997).
Bhattacharjee, Y., "More Than the Patch: New Ways to Take Medicine Via Skin," *New York Times*, Jul. 2, 2002, p. F5.
Brannon-Peppas, L., "Polymers in Controlled Drug Delivery," *Medical Plastics and Biomaterials Magazine*, Nov. 1997.
Cevc, G. et al, Transdermal Drug Carriers: Basic Properties, Optimization and Transfer Efficiency in the Case of Epicutaneously Applied Peptides, *Journal of Controlled Release* 36: 3-16 (1995).
Chetty, D. and Chien, Y., Novel Methods of Insulin Delivery: An Update, *Critical Reviews in Therapeutic Drug Carrier Systems*, 15(6): 629-670 (1998).
Christie, W.W., Phosphatidylcholine and Related Lipids, www.lipid.co.uk, May 5, 2003.
Daddona, P., Recent Advances in Peptide, Protein and Macromolecule Drug Delivery, *Current Opinion in Drug Discovery & Development*, 2(2): 168-171 (19999).
Daniels, R., "Galenic Principles of Modern Skin Care Products," *Skin Care Forum*, Issue 25, Apr. 2001.
Guo et al, "Transdermal Delivery of Insulin in Mice by Using Lecithin Vesicles as a Carrier," *Drug Delivery*, 7:113-116 (2000).
Mitragotri, S., "Synergistic Effect of Enhancers for Transdermal Drug Delivery," *Pharmaceutical Research*, 17(11):1354-1359 (2000).
Patki, V.P. and Jagasia, S.H., "Progress Made in Non-Invasive Insulin Delivery," *Indian Journal of Pharmacology*, 28:143-151 (1996).
Trehan, A. and Ali, A., "Recent Approaches in Insulin Delivery," *Drug Development and Industrial Pharmacy*, 24(7): 589-97 (1998).

* cited by examiner

*Primary Examiner*—Johann Richter
*Assistant Examiner*—Ernst V Arnold
(74) *Attorney, Agent, or Firm*—St. Onge Steward Johnston & Reens LLC

(57) ABSTRACT

A stable composition of a drug comprising a carrier having a phosphatidylcholine component which entraps the drug is applied to the skin for transdermal delivery of the drug.

19 Claims, No Drawings

STABLE TOPICAL DRUG DELIVERY COMPOSITIONS

PRIOR APPLICATION

This application is a continuation-in-part of U.S. patent application Ser. No. 10/448,632 filed May 30, 2003, which application is currently pending, and which claims priority to U.S. Provisional Patent Application No. 60/384,597, filed May 31, 2002. Applicant claims priority benefits under 35 U.S.C. §119(e) of U.S. Provisional Patent Application Ser. No. 60/437,279 filed Dec. 31, 2002.

FIELD OF THE INVENTION

The present invention relates to topical drug delivery compositions and methods of transdermal drug delivery. More specifically, the present invention relates to stable drug delivery compositions for topical administration.

BACKGROUND OF THE INVENTION

Topical drug delivery systems are known. These systems deliver drugs, therapeutic agents and other desired substances transdermally and may be designed to act locally at the point of application or to act systemically once entering the body's blood circulation. In these systems, delivery may be achieved by means such as direct topical application of a substance or drug in the form of an ointment or the like, or by adhesion of a patch with a reservoir or the like that holds the drug and releases it to the skin in a time-controlled fashion.

Transdermal delivery systems for agents such as drugs, pain relieving compounds, vitamins, and skin improving compounds have been in use for a number of years. These transdermal delivery systems using creams have been developed for use with analgesics and skin refining compounds. Transdermal systems using a patch have been developed for nicotine and estrogen therapies, for instance, estradiol technology described in U.S. Pat. No. 6,521,250 to Meconi, et al.

While effective for their purpose, these systems have typically only been useful for transdermal delivery of relatively small molecules. The skin's porous structure permits such small molecules to pass from the epidermis to the dermis via diffusion. However, large molecules, such as insulin, are not able to diffuse through the skin and cannot be delivered by these known means. One such solution has been provided in U.S. patent application Ser. No. 10/448,632 filed on May 30, 2003 to Perricone, the disclosure of which is incorporated herein by reference.

While the delivery of large molecules such as insulin have been addressed, such systems do not address the storage and retention of the effectiveness of the drug to be delivered. Many pharmaceuticals and biologically active compounds, such as insulin, must be kept cool and away from heat to remain effective and prevent denaturing at ambient temperatures. Such substances may not be stored or carried (without refrigeration) by the user. Often drugs like insulin must be administered throughout the day and should be in ready-access to or carried by the user, which may expose the compound to high temperatures. As such, there remains a need to stabilize compositions, including insulin, so that they are resistant to warmer temperatures and have a longer life at these temperatures without a need for refrigeration

SUMMARY OF THE INVENTION

A composition for transdermal delivery of a macromolecule comprises a phosphatidylcholine carrier component entrapping the macromolecule, wherein the carrier component stabilizes the macromolecule at room temperature.

A method for administering a drug or other active agent comprises applying to skin composition containing an effective amount of the drug or active agent, a carrier having a phosphatidylcholine component entrapping the drug or active agent.

DETAILED DESCRIPTION OF THE INVENTION

Phosphatidylcholine is used as a carrier for the topical delivery of polypeptides and macromolecules in the practice of this invention. Phosphatidylcholine is a basic component of cell membrane bilayers and the main phospholipid circulating in the plasma. Phosphatidylcholine is highly absorbable and supplies choline which is needed to facilitate movement of fats and oils across and maintain cell membranes in animals.

Topical delivery compositions of the present invention are non-polar and formulated to contain polypeptides and macromolecules soluble in phosphatidylcholine, which are then applied to skin for transdermal delivery of the macromolecule. Topical delivery compositions of the invention are efficacious in the delivery of macromolecular drugs that are conventionally administered intramuscularly, intravenously or orally, including, but not limited to polypeptides such as insulin and somatropin, prostaglandins, glucocorticoids, estrogens, androgens, and the like.

It is an advantage of the invention that topical administration of a composition and transdermal delivery of the drug or active agent therein is easier and pleasanter as an administration route than injections, particularly for drugs such as insulin that must be given to patients over a period of time, or for a lifetime. Furthermore, unlike oral administration where a substantial amount of the drug can be destroyed in the digestive process, the drugs in a topical application are not wasted. Topical application allows a steady diffusion of the drug to the desired target area without the cyclic dosages typical of orally or parenterally administered drugs.

The term "phosphatidylcholine" as used herein means a mixture of stearic, palmitic, and oleic acid diglycerides linked to the choline ester of phosphoric acid, commonly called lecithin. Many commercial lecithin products are available, such as, for example, Lecithol®, Vitellin®, Kelecin®, and Granulestin® because lecithin is widely used in the food industry. Compositions of the invention can contain synthetic or natural lecithin, or mixtures thereof. Natural preparations are preferred because they exhibit desirable physical characteristics and are both economical and non-toxic.

Preferred topical delivery compositions of the present invention additionally contain polyenylphosphatidylcholine (herein abbreviated "PPC") to enhance epidermal penetration. The term "polyenylphosphatidylcholine" as used herein means any phosphatidylcholine bearing two fatty acid substituents, wherein at least one is an unsaturated fatty acid with at least two double bonds such as linoleic acid. Certain types of soybean lecithin and soybean fractions, for example, contain higher levels of polyenylphosphatidylcholine, with dilinoleoylphosphatidylcholine (18:2—18:2 phosphatidylcholine) as the most abundant phosphatidylcholine species, than conventional food grade lecithin, and are useful in formulating topical delivery compositions of the invention. Alternatively, conventional soybean lecithin is enriched with polyenylphosphatidylcholine by adding soybean extracts containing high levels of polyenylphosphatidylcholine. As used herein, this type of phosphatidylcholine is called "polyenylphosphatidylcholine-enriched" phosphatidylcholine (hereinafter referred to as PPC-enriched phosphatidylcholine), even where the term encompasses lecithin obtained from natural sources exhibiting polyenylphosphatidylcholine levels higher than ordinary soybean varieties. These products are commercially available from American Lecithin Company, Rhône-Poulenc and other lecithin vendors. American Lecithin Company markets its products with a "U" designation, indicating high levels of unsaturation; Rhône-Poulenc's product is a soybean extract containing about 42% dilinoleoylphosphatidylcholine and about 24% palmitoyllinoleylphosphatidylcholine (16:0–18:2 PC) as the major phosphatidylcholine components.

While not wishing to be bound to any theory, it is believed that the PPC-enriched phosphatidylcholine forms a bilayer enveloping the polypeptide or macromolecule to create the topical drug delivery composition, contributing to the stability of the active molecule and enhancing penetration. Further, the topical drug delivery composition may be in liquid crystal phase, with the PPC-enriched phosphatidylcholine loosely arranged in multilamellar fashion, with the polypeptide or macromolecule being bonded and entrapped within the lipid bilayers formed therein, as disclosed in U.S. patent application Ser. No. 10/448,632 filed on May 30, 2003 to Perricone. This forms a loosely arranged, yet stable, PPC-enriched phosphatidylcholine-drug complex that further increases penetration and delivery of the polypeptide or macromolecule to the dermal vasculature.

Topical drug delivery compositions of the present invention provide an administration route that is a marked improvement over conventional insulin injections, considerably easier and pleasanter. It is a further advantage that compositions of the invention are also stable at room temperature, providing considerable convenience for insulin users who, in the past, have had to deal with the refrigerated insulin products commercially available. Also, insulin compositions according to the present invention have longer shelf lives (whether stored at room temperature or refrigerated) and will not denature at room temperature as would traditional insulin treatments.

Insulin useful in the topical drug delivery compositions of the present invention is commercially available from a variety of sources, marketed under the tradenames Humulin®, Novolin®, Humalog®, Inutral®, among others. Some of these products contain porcine sequences. Compositions of the invention are preferably formulated with recombinant human polypeptides such as those obtained from Sigma Co., Spectrum Chemicals and Laboratories, and similar vendors and employed in the examples that follow. It is an advantage of the invention that topical drug delivery compositions carrying insulin are formulated with commercially available ingredients.

Topical drug delivery compositions are generally formulated with a carrier comprising a PPC-enriched phosphatidylcholine material with the trade name NAT 8729 (commercially available from vendors such as Rhône-Poulenc and American Lecithin Company and at least one polyglycol (polyhydric alcohol of a monomeric glycol such as Polyethylene glycol (PEG) 200, 300, 400, 600, 1000, 1450, 3350, 4000, 6000, 8000 and 20000). Further, this carrier may comprise a surfactant such as a siloxylated polyether comprising dimethyl, methyl(propylpolyethylene oxide propylene oxide, acetate) siloxane commercially available from vendors such as Dow Corning (Dow Corning 190 surfactant) and lubricant such as silicone fluids containing low viscosity polydimethylsiloxane polymers, methylparaben (p-hydroxy benzoic acid methyl ester) commercially available from vendors such as Down Corning (Dow Corning 200 silicone fluid). Additionally, purified water may be added to the carrier. The carrier is then mixed with a preparation of the particular polypeptide(s) or macromolecule(s) in an amount to obtain the desired strength in the final composition. The following examples are presented to further illustrate and explain the present invention and should not be taken as limiting in any regard.

Preparation of Stable Insulin Compositions:
Example 1

Stable insulin topical preparations were formulated by first preparing a base solution. A polyenylphosphatidylcholine material denoted NAT 8729 which contained 80.6% PPC-enriched phosphatidylcholine and 4.9% lysophosphatidylcholine was obtained from Rhône-Poulenc. NAT 8729 (45% w/w) was shaved and added to a mixture of polyglycol E200 (50% w/w) and polyglycol E400 (5% w/w) both obtained from Dow Corning. The base solution was then covered well and lightning mixed with a special disintegration head impeller slowly at 800 rpm with slight heat. The temperature did not go above 40° C. Typical mixing times were 5 hours. The final solution is a crystal clear, viscous amber solution with no sediments or separations.

Into this base solution (97.25% w/w) was then mixed a Dow Corning Fluid 190 (1.00% w/w) [a siloxylated polyether comprising dimethyl, methyl(propylpolyethylene oxide propylene oxide, acetate) siloxane]; a Dow Corning silicone fluid denoted 200-5 or 10 cst (1.00% w/w) [silicone fluids containing low viscosity polydimethylsiloxane polymers]; and methylparaben [p-hydroxy benzoic acid methyl ester] obtained from Mallinckrodt (0.75% w/w). The ingredients were homogenized with 3850 rpm with a 0.45 micron screen as follows. The methylparaben was first added to the base solution and mixed for at least an hour until a complete solution formed. Then the Dow Corning 200-5 or 10 cst was slowly added and mixed until a clear solution formed. Afterwards the Dow Corning Fluid 190 was added slowly and mixed into the solution to form the carrier.

Insulin preparations of the invention were then made using the carrier in two strengths: 50 units and 100 units, by simply dissolving RNA-derived recombinant human insulin obtained from Sigma into the carrier. It was readily soluble in the carrier.

In testing the stability of the stable insulin composition, insulin standards were prepared at 1 mg/ml in 0.01 N HCl using Sigma insulin. (One mg of this material exhibits an activity of 28 insulin units.) Stable insulin compositions samples were prepared at 1 mg/1 ml base by mixing at room temperature for 60 minutes. This mixture was then divided in half, half of which was stored at 4° C., and the other half stored at room temperature. Separation analyses, High Performance Liquid Chromatography (RP-HPLC) and High Performance Capillary Electrophoresis (HPCE), of insulin standards and insulin compositions of the invention which were stored at different temperatures for different periods of time were performed.

The RP-HPLC and HPCE analyses indicated that insulin standards that were stored at 4° C. or −20° C. were stable after 65 days, but insulin standards stored at room temperature started to denature within 7 days. The RP-HPLC and HPCE profiles of insulin compositions of the invention, on the other hand, were stable at both room temperature and at 4° C., and did not change after 65 days. The results clearly showed that the carrier prevented the denaturing of the insulin stored at room temperature.

Preparation of Stable Insulin Compositions:
Example 2

Stable insulin compositions were formulated by first preparing a base solution. Polyglycol E200 (PEG-200) (50% w/w) was weighed and polyglycol E400 (PEG-400) (5% w/w) was added to the same container to obtain the desired weight, (both obtained from Dow Corning). PEG-200 and PEG-400 were lightning mixed at 38–40° C. with IKA model RW20 using a disintegration head impeller slowly at 800 rpm (speed 1), yielding PEG-200/PEG-400 solution. A PPC-enriched phosphatidylcholine material denoted NAT 8729 containing 80.6% PPC-enriched phosphatidylcholine and 4.9% lysophosphatidylcholine was obtained from Rhône-Poulenc. NAT 8729 (45% w/w) was shaved and added to PEG-200/PEG-400 solution, covered and mixed, with temperature not exceeding 40° C., until a clear, viscous amber solution with no sediments or separations resulted. The mixing time was approximately five hours. An alternative mixture can be prepared by covering and mixing the solution overnight without heat for a 95–96% yield. The solution was removed from heat and transferred to Ross Homogenizer (Model HSM100LC) using smallest mesh screen.

A Dow Corning Fluid was then prepared. Dow Corning Fluid denominated 190 (1.00% w/w) [a siloxylated polyether comprising dimethyl, methyl(propylpolyethylene oxide propylene oxide, acetate) siloxane] and Dow Corning Fluid denoted 200-5 or 10 cst (1.00% w/w) [silicone fluids containing low viscosity polydimethylsiloxane polymers] were mixed together in a container with a clean spatula.

The solution (53.25% w/w) was warmed to 40° C. and mixed at 800 rpm. Typical mixing times were approximately 5 hours. The solution was then milled at 3800 rpm and the Dow Corning Fluid mixture was added very slowly until the a clear solution resulted. Methyl Paraben (p-hydroxy benzoic acid methyl ester) obtained from Mallinckrodt (0.75% w/w) was added at once and mixed until a complete solution resulted. Purified water warmed to 40° C. was added very slowly to solution while milling at 7500 rpm for about three minutes. At end of milling, speed was increased to 10,000 rpm for few seconds before stopping. The solution was removed and swept with paddle head using IKA Model RW-20 until cooled to room temperature. This step is very critical and if it is not done properly it will generate a biphasic end product. The general rule is to use a container having a volume twice that of the solution so the homogenizer head is well embedded in the solution. The solution was then cooled to room temperature.

USP human recombinant insulin in obtained from Spectrum Chemicals and Laboratories (Product #11247) was prepared in 0.01 N HCl at 50 mg/ml, and gently, yet well mixed. This insulin preparation was then added very slowly to the above solution to obtain a final concentration of 500 units/ml or 20 mg/ml. Mixing was continued at room temperature for at least one hour. The final stable insulin composition was stored at 4° C. in amber air-tight container.

RP-HPLC and HPCE analyses of insulin standards (prepared at 5 mg/ml in 0.01 N HCl) and stable insulin compositions of the invention which were stored at different temperatures for different periods of time were performed. The results indicated that standard insulin standards stored at 4° were stable up to 22 weeks and started to denature after 34 weeks, whereas when stored at room temperature started to denature within only 1 week. However, the stable insulin compositions prepared in accordance with the above disclosures that were stored at room temperature were stable up to at least 22 weeks, which is 21 weeks longer than the standard. The results showed no change in shelf-life from the standard for stable insulin compositions stored at 4° C. (no change after 34 weeks).

Stable topical drug delivery compositions of the present invention may be employed to deliver and stabilize polypeptides transdermally, including but not limited to insulin, oxytocin, vasopressin, insulin, somatotropin, calcitonin, choriomic gonadotropin, menotropins, follitropins, somatostatins, progestins, and combinations of any of these. These drugs are readily available from a variety of commercial sources. Somatotropin (pituitary growth hormone) is marketed under the tradenames Gentropin®, Humatrope®, Nutropin®, and Serostim®.

A drug delivery composition formulated with somatotropin was formulated in one trial with 85% phosphatidylcholine to which lipoic acid and ascorbyl palmitate were added. Somatotropin readily dispersed in phosphatidylcholine and remained stable in it. Growth hormone appeared to penetrate the skin well when the composition was topically applied.

The present invention may also be used to provide topical delivery of active agents other that drugs, for example, skin care agents. The invention is particularly useful with large molecules that are used in some cosmetic formulations, including peptides and polymers.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention

What is claimed is:

1. A carrier composition for transdermal delivery of a macromolecule, comprising a polyenylphosphatidylcholine-enriched phosphatidyicholine component entrapping said macromolecule for transdermal delivery to dermal vasculature, wherein said phosphatidyicholine component stabilizes said macromolecule at room temperature and wherein said polyenylphosphatidylcholine-enriched phosphatidylcholine component further comprises a polyglycol having molecular weight of 200 and a polyglycol having molecular weight of 400.

2. The composition of claim 1, wherein said polyenylphosphatidylcholine-enriched phosphatidylcholine component comprises 45% w/w polyenylphosphatidylcholine-enriched phosphatidylcholine, 50% w/w polyglycol having molecular weight of 200, and 5% w/w polyglycol having molecular weight of 400.

3. The composition of claim 1, further comprising a surfactant, a lubricant, and methyl paraben.

4. The composition of claim 3, comprising 97.25% w/w polyenylphosphatidylcholine-enriched phosphatidylcholine component, 1.00% w/w surfactant, 1.00% w/w lubricant, and 0.75% w/w methyl paraben.

5. The composition of claim 3, further comprising water.

6. The composition of claim 5, comprising 53.25% w/w polyenylphosphatidylcholine-enriched phosphatidyicholine component, 1.00% w/w surfactant, 1.00% w/w lubricant, 0.75% w/w methyl paraben and 44% w/w water.

7. The composition of claim 3, wherein said surfactant is a siloxylated polyether.

8. The composition of claim 3, wherein said lubricant is silicone fluid.

9. The composition of claim 8, wherein said silicone fluid contains low viscosity polydimethylsiloxane polymers.

10. The composition of claim 1, wherein said macromolecule is selected from the group consisting of oxytocin, vasopressin, insulin, somatotropin, calcitonin, chorionic gonadotropin, menotropins, follitropins, somatostatins, progestins, peptides, polymers, and combinations thereof.

11. A stable topical insulin composition, comprising:
carrier having a polyenylphosphatidylcholine-enriched phosphatidyicholine component, said polyenylphosphatidylcholine-enriched phosphatidylcholine component including a polyglycol having molecular weight of 200 and a polyglycol having molecular weight of 400, and
insulin entrapped within said carrier for transdermal delivery of the insulin to dermal vasculature.

12. The composition of claim 11, wherein said phosphatidylcholine component comprises 45% w/w polyenylphosphatidylcholine-enriched polyenylphosphatidylcholine, 50% w/w polyglycol having molecular weight of 200, and 5% w/w polyglycol having molecular weight of 400.

13. The composition of claim 11, wherein said carrier further comprises a surfactant, a lubricant, and methyl paraben.

14. The composition of claim 13, wherein said carrier comprises 97.25% w/w polyenylphosphatidylcholine-enriched phosphatidylcholine component, 1.00% w/w surfactant, 1.00% w/w lubricant, and 0.75% w/w methyl paraben.

15. The composition of claim 11, wherein said carrier further comprises water.

16. The composition of claim 11, wherein said carrier comprises 53.25% w/w polyenylphosphatidylcholine-enriched phosphatidylcholine component, 1.00% w/w surfactant, 1.00% w/w lubricant, 0.75% w/w methyl paraben and 44% w/w water.

17. The composition of claim 13, wherein said surfactant is a siloxylated polyether.

18. The composition of claim 17, wherein said lubricant is silicone fluid.

19. The composition of claim 18, wherein said silicone fluid contains low viscosity polydimethylsiloxane polymers.

* * * * *